United States Patent [19]
Gross et al.

[11] Patent Number: 5,090,963
[45] Date of Patent: Feb. 25, 1992

[54] ELECTROCHEMICALLY DRIVEN METERING MEDICAMENT DISPENSER

[75] Inventors: Joseph Gross, Moshav Mazor; Shlomo Zucker, Yavne, both of Israel

[73] Assignee: Product Development (Z.G.S.) Ltd., Petach Tiqua, Israel

[21] Appl. No.: 599,917

[22] Filed: Oct. 19, 1990

[51] Int. Cl.$^5$ .......................................... A61M 37/00
[52] U.S. Cl. ........................... 604/132; 604/141; 604/145; 222/105; 222/494; 128/DIG. 12
[58] Field of Search ............... 222/95, 105, 386.5, 222/494, 491, 83.5, 83; 604/132–148, 153, 891.1; 128/DIG. 12

[56] References Cited

U.S. PATENT DOCUMENTS

| | | | |
|---|---|---|---|
| 2,766,907 | 10/1956 | Wallace, Jr. | 222/45 X |
| 3,115,280 | 12/1963 | Battista | 222/95 |
| 3,894,538 | 7/1975 | Richter | 222/95 X |
| 4,624,393 | 11/1986 | Lopez | 222/83.5 |
| 4,639,244 | 1/1987 | Rizk et al. | 604/891.1 X |
| 4,820,273 | 4/1989 | Reinickle | 128/DIG. 12 |
| 4,886,514 | 12/1989 | Maget | 604/891.1 |
| 4,902,278 | 2/1990 | Maget et al. | 604/891.1 X |
| 4,968,301 | 11/1990 | di Palma et al. | 128/DIG. 12 |
| 4,978,036 | 12/1990 | Burd | 222/494 X |

Primary Examiner—Michael S. Huppert
Assistant Examiner—Kenneth DeRosa
Attorney, Agent, or Firm—Benjamin J. Barish

[57] ABSTRACT

A liquid material dispenser includes a rigid housing having a flexible partition defining first and second compartments on opposite sides of the partition, and an electrolytic cell in the first compartment capable of generating a gas when energized by a source of electric current in order to expand the first compartment and thereby to contract the second compartment. The second compartment contains the liquid material which is dispensed via a discharge opening in accordance with the rate of generation of the gas.

17 Claims, 3 Drawing Sheets

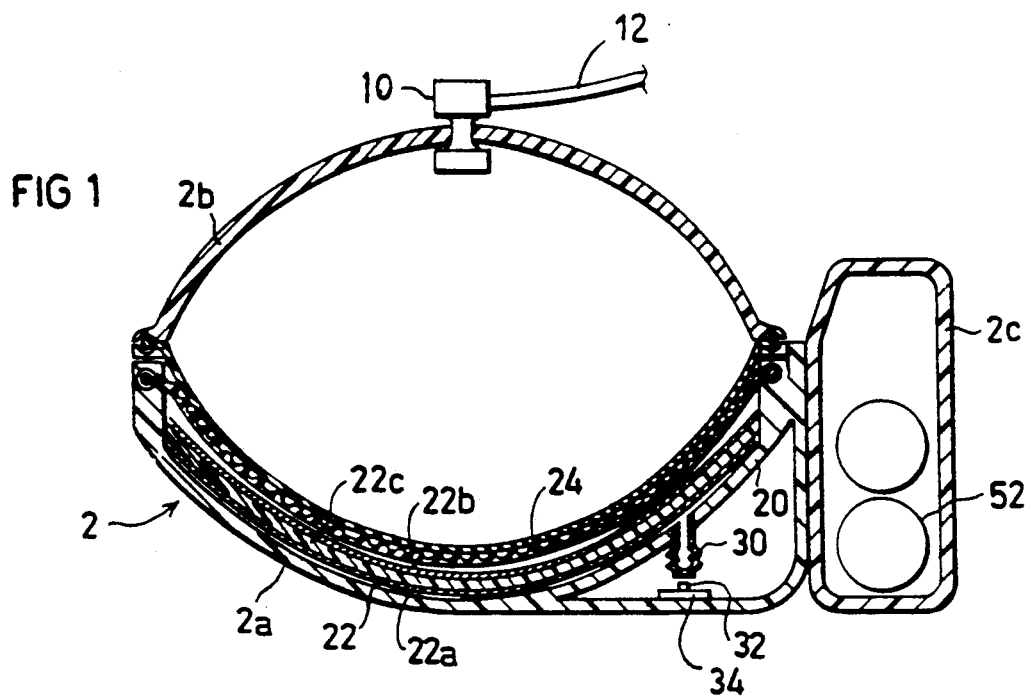
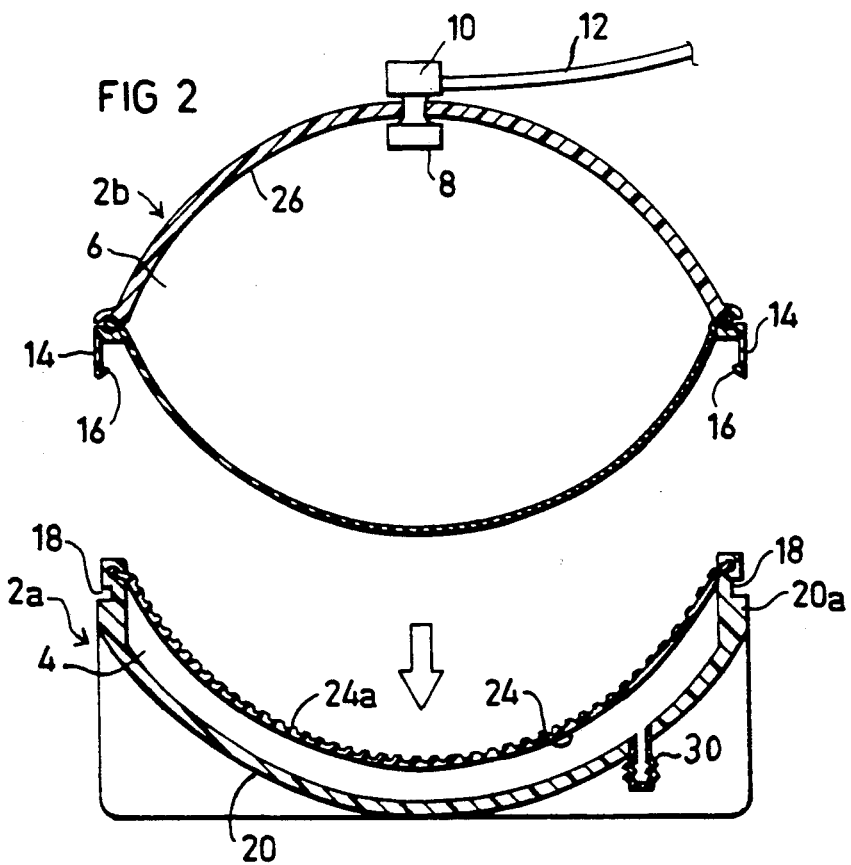

ELECTROCHEMICALLY DRIVEN METERING MEDICAMENT DISPENSER

FIELD AND BACKGROUND OF THE INVENTION

The present invention relates to a dispenser for dispensing a liquid material. The invention is particularly useful for dispensing medicaments at small, precisely-controlled rates, and is therefore described below with respect to this application.

There are many applications requiring the dispensing or delivering of a liquid at predetermined, precisely-controlled rates. One application requiring particularly precise rates of delivery is a system for administering insulin or other medicaments, and very precise miniature pumps have been devised for this purpose. However, such pumps are expensive to produce and maintain, and/or are inconvenient to refill with the periodic dosage requirements.

It has been previously proposed, particularly in such applications, to use an arrangement for subjecting the liquid to a pressurized gas to force the liquid from the container. Examples of such known systems are illustrated in U.S. Pat. No. 3,640,277 disclosing a gas cartridge for supplying the gas pressure, U.S. Pat. No. 3,468,308 disclosing an inflated bladder for supplying the gas pressure, U.S. Pat. No. 3,871,553 connectible to a compressed air hose for supplying air pressure, and U.S. Pat. No. 2,545,017 disclosing an arrangement for generating the gas by a chemical reaction. Such arrangements, however, generally suffer from the same drawbacks mentioned earlier, namely expensive to produce and maintain, and/or inconvenient to refill. In addition, such known arrangements generally require a valve which must be precisely controlled in order to control the rate of delivery of the liquid to be dispensed; and precise control is extremely difficult when very low rates of delivery are required as in the case of the delivery of insulin or other types of medicaments.

OBJECTS AND SUMMARY OF THE PRESENT INVENTION

An object of the present invention is to provide a liquid material dispenser having advantages in some or all of the above respects. Particular objects are to provide a dispenser which is safe and which includes a few simple parts producible in volume and at low cost, and which therefore may be constructed and supplied as disposable devices for one-time use.

According to the present invention, there is provided a liquid material dispenser, comprising a rigid housing having a flexible partition therein defining first and second compartments on opposite sides of the partition; an electrolytic cell in the first compartment capable of generating a gas when energized by a source of electric current in order to expand the first compartment and thereby to contract the second compartment. The second compartment contains the liquid material and, upon its contraction, dispenses the liquid material via a discharge opening in accordance with the rate of generation of the gas.

According to further features in the preferred embodiments of the invention described below, the rigid housing is made of two separable sections each for housing one of the compartments. In addition, each of the two housing sections contains a membrane. The two membranes contact each other when the two sections are attached in the operative condition of the dispenser and together constitute the flexible partition. At least one of the membranes is formed with protrusions facing the other membrane to define a space between the two membranes, which space is vented to the atmosphere to prevent any gas generated in the first compartment from entering the second compartment.

According to still further features in the preferred embodiments of the invention described below, the two housing sections are attachable to each other by a snap-on connection including projections carried by one of the sections snappable into recesses formed in the other of the sections. In addition, the first compartment carries a sensor for sensing a predetermined maximum expansion of the first compartment and is effective, in response thereto, to terminate the further electrical energization of the electrolytic cell.

According to still further features in the described preferred embodiments, the second compartment includes a control valve comprising a valve member and a spring normally urging the valve member to close the discharge opening, the valve member being movable to its open position upon the generation of pressure in the second compartment sufficient to overcome the force of the spring.

According to a still further feature in the described preferred embodiments, the first compartment comprises a wall pierceable by the needle of a syringe filled with air for introducing air into the first compartment in order to purge the second compartment of air when priming the dispenser. In addition, the second compartment may further include a venting opening permeable by air but not by liquid.

According to still further features in the described preferred embodiment, the housing further includes a power supply and control circuitry for controlling the energization of the electrolytic cell. Thus, the control circuitry may include a preprogrammable processor for preprogramming the rates and times of energization of the electrolytic cell, and thereby of the dispensing of the liquid material from the second compartment.

It will be seen that a liquid material dispensers constructed in accordance with some or all of the foregoing features enable precise control of the rate and time of dispensing of the liquid material, are inexpensive to produce and maintain, and permit convenient refilling thereby making them particularly suitable for use in dispensing medicaments, such as insulin, but also useful in many other applications.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates one form of dispenser constructed in accordance with the present invention;

FIG. 2 is an exploded view illustrating the main elements of the dispenser of FIG. 1;

DESCRIPTION OF PREFERRED EMBODIMENTS

Figure 3:
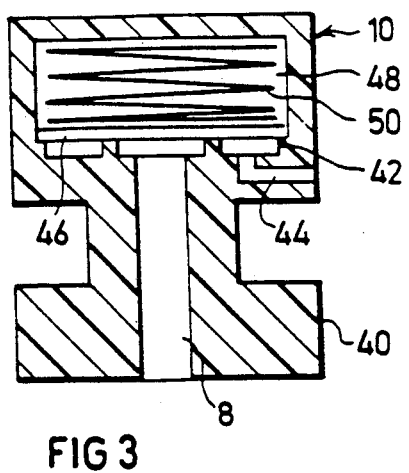
FIG. 3 is an enlarged sectional view illustrating the construction of the relief valve at the discharge opening in the dispenser of FIGS. 1 and 2.

The dispensers illustrated in the drawings are intended primarily for dispensing medicaments, such as insulin, chemotherapeutic drugs, antibiotics, pain-relief drugs, etc., at precisely-controlled, slow rates. The illustrated dispensers are designed to be worn on the body of the user and to enable ready refilling with the medicament to be dispensed.

The dispenser illustrated in FIGS. 1 and 2 comprises a housing, generally designated 2, made of two sections 2a, 2b quickly attachable together as shown particularly in FIG. 2. Section 2a includes a first compartment 4 for receiving an electrolytic cell capable of generating a gas when energized by a source of electric current; and housing section 2b includes a second compartment 6 for receiving the liquid material (e.g., medicament) to be dispensed via an outlet opening 8 and a control valve 10 to a feed tube 12. As shown particularly in FIG. 2, housing section 2b includes a plurality (e.g., two) flexible fingers 14 each terminating in a projection 16, which projections are snappable into an annular recess 18 formed in the upper part of the lower housing section 2a.

Housing section 2a is of rigid material. It includes a lower rigid wall 20 of concave configuration defining the lower end of the compartment 4 containing the electrolytic cell. As shown in FIG. 1, electrolytic cell, generally designated 22, comprises two spaced electrodes 22a, 22b separated by an electrolyte 22c. The upper end of compartment 4 is defined by a membrane 24 which is also of concave configuration in its normal condition but which is flexed outwardly, thereby expanding chamber 4, when a gas is generated in the electrolyte 22c by the passage of electric current through it from the two electrodes 22a, 22b. As one example, the two electrodes 22a, 22b may each be a flexible stainless steel screen, whereas the electrolyte 22c may be an 8% solution of sodium bicarbonate ($NaHCO_3$) in water, or a 4% solution of copper sulphate($CuSO_4$) in water.

Housing section 2b includes a rigid upper wall 26 of convex configuration, and a lower wall 28 in the form of a flexible membrane, to define the compartment 6 for receiving the liquid material to be dispensed. When compartment 6 is filled with the liquid material, the membrane 28 assumes a convex configuration as illustrated in FIG. 2 so as to complement the concave configuration of membrane 24 in the lower housing section 2a. When housing section 2b is attached to housing section 2a, the two membranes 24 and 28 come into contact with each other and define a flexible partition, constituted of the two membranes 24 and 28, separating the electrolytic cell compartment 4 in section 2a from the medicament compartment 6 in section 2b.

As shown particularly in FIG. 2, the upper surface of membrane 24 in the lower housing section 2a is formed with a plurality of protrusions or ribs 24a facing membrane 28 of housing section 2b. These protrusions 24a define a space between the two membranes 24, 28, which space is vented to the atmosphere, and thereby prevents any gas generated in the electrolytic cell compartment 4 from entering the medicament compartment 6 should the gas from compartment 4 somehow permeate through membrane 24.

The dispenser illustrated in FIG. 1 further includes a sensor for sensing a predetermined maximum pressure in the electrolytic cell compartment 4 to terminate the further electrical energization of the electrolytic cell. Thus, as shown in FIGS. 1, the rigid lower wall 20 of compartment 4 includes an expansible chamber in the form of a bellows 30 whose interior communicates with compartment 4. The outer end of bellows 30 is aligned with, but normally spaced from, an operator 32 of an electrical switch 34, such that when the pressure within compartment 4 rises to a predetermined magnitude, its lower end engages operator 32 to operate switch 34 and thereby to terminate the energization of the electrolytic cell 22 within compartment 4. Bellows 30 and electrical switch 34 controlled thereby, may therefore be used to regulate the pressure developed within the electrolytic cell chamber 4 to produce a relatively constant rate of dispensing of the liquid from chamber 6, as well as for automatically terminating the operation of the dispenser when all the liquid has been dispensed from chamber 6.

The control valve 10 between the discharge opening 8 of the medicament chamber 6 and the feed tube 12 establishes a predetermined control pressure in the chamber fixing the feeding rate of the medicament. Valve 10 also prevents a rapid siphonic flow of the medicament through the feed tube should, for example, the outlet end of the feed tube be located below the medicament compartment. As shown in FIG. 3, control valve 10 includes a housing 40 formed with a central bore constituting the outlet opening 8, and with an annular recess 42 surrounding the central bore. A second bore 44 communicates with the recess 42 and with the feed tube 12 when attached to the control valve 10.

A valve member, in the form of a flat plate or disc 46, is included within a chamber 48 formed within the valve housing 40, and is urged by a spring 0 to cover both the central bore 8 and the annular recess 42. Thus, valve member 46 blocks the flow of the medicament from medicament compartment 6 to the feed tube 12, but when pressure is built up within the medicament compartment by the generation of gas in the electrolytic-cell compartment 4, this pressure moves valve member 46 so as to establish communication between bore 8 and recess 42, permitting the medicament to flow from compartment 6 to the feed tube 12.

Housing 2 includes a third section 2c, preferably integrally formed with the lower housing section 2a, for housing the batteries 52 and other control circuitry (not shown) which may be needed in order to energize the electrodes 22a, 22b of the electrolytic cell 22 within compartment 4.

A portion of the wall 20, as shown at 20a FIG. 2, or the complete wall 20, is made of a material (e.g., rubber) which is pierceable by the needle of a syringe (not shown) filled with air for introducing air into the electrolytic-cell compartment 4 in order to purge the medicament compartment 6 of air when priming the dispenser.

Figure 4:
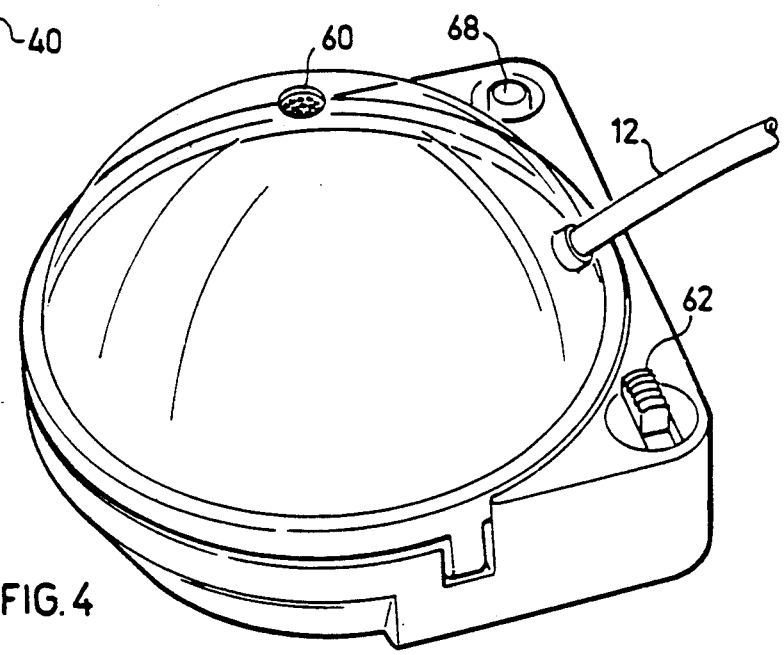
FIGS. 4 and 5 are perspective views illustrating other forms of dispensers constructed in accordance with the invention.

FIG. 4 illustrates a variation, wherein the batteries (not shown) are not disposed within a separate housing section (section 2c, FIG. 1), but rather are disposed within the housing section 2a containing the electrolytic-cell compartment 4. In addition, the medicament compartment 6 includes, not only the outlet port connected to the feed tube 12, but also a venting port 60 which includes material, e.g., a hydrophobic filter, permeable by air and not by liquid.

In order to prime the dispenser, the needle of a syringe (not shown) filled with air is applied to pierce section 20a of wall 20 and to introduce air into the electrolytic-cell compartment 4, to expand that compartment and thereby to contract the medicament compartment 6, until all the air is purged from compartment 6. Since venting port 60 is permeable by air, the air within compartment 6 will be able to pass out; but as soon as all the air has been exhausted, a resistance will be presented to the contraction of compartment 6, and thereby to the injection of additional air into compartment 4, indicating to the user that the dispenser has been primed and is ready for use.

The dispenser illustrated in FIG. 4 further includes an on/off switch 62 for energizing the electrolytic cell to effect the dispensing of the liquid, at a predetermined rate, and a bolus button 68 which may be depressed to effect a rapid dispensing of the liquid.

Figure 5:
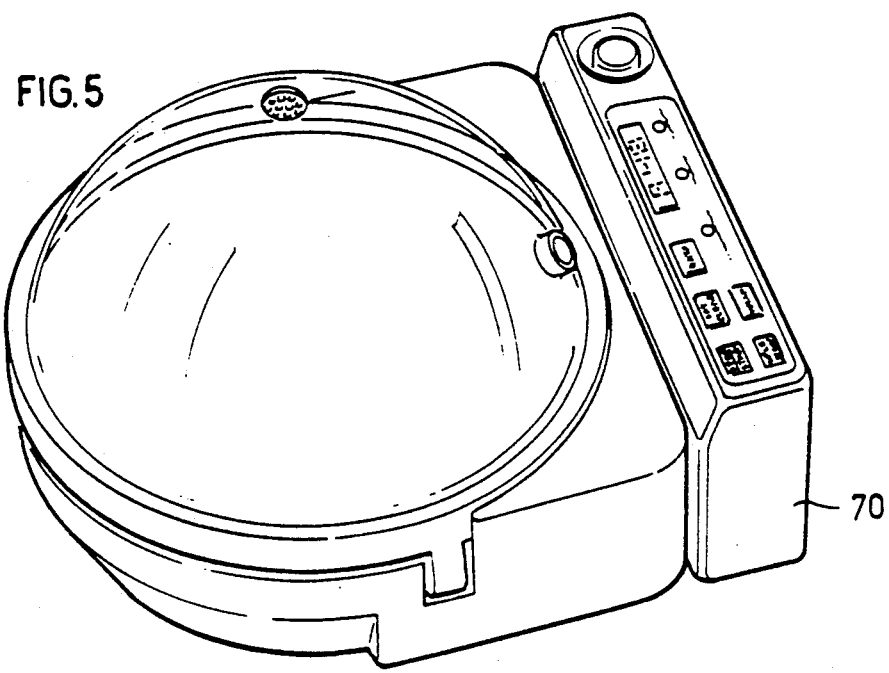

FIG. 5 illustrates another variation in the construction of the dispenser, wherein the housing further includes a power supply and a control circuit, housed within housing section 70. The latter housing section includes a preprogrammable processor for preprogramming the rates and times of energizing the electrolytic cell, and thereby of dispensing the liquid from the medicament compartment 6 to the patient.

Figure 6:
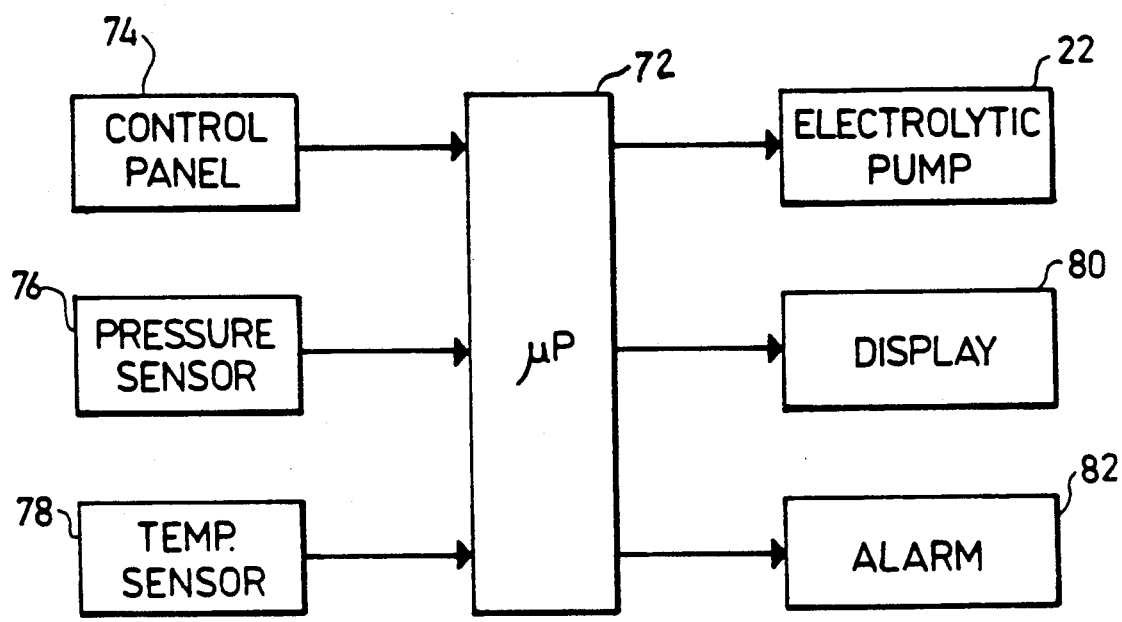
FIG. 6 is a block diagram illustrating the main electrical components in the dispenser of FIG. 5.

FIG. 6 is a block diagram illustrating one form of control circuit which may be used in the embodiment of FIG. 5. The control circuit includes a microcontroller 72 which receives inputs from the control panel 74 and a pressure sensor 76, e.g., the bellows 30 and electrical switch 34 controlled thereby illustrated in FIG. 1. The dispenser may also include a temperature sensor 78 for sensing the temperature of the gas in compartment 6 generated by the electrolytic cell 22, since the temperature also influences the rate of energization of the electrolytic cell in order to produce a predetermined expansion of compartment 6.

The microcontroller 72 in turn controls the current supplied to the electrolytic cell 22, serving as a pump and therefore identified by block 22 in FIG. 6. The microcontroller 72 may also control one or more displays 80 and/or alarms 82.

The operation of the illustrated dispensers will be apparent from the above description.

Thus, housing section 2b, whose compartment 6 is filled with the medicament to be dispensed, is snapped-on by fingers 14 to housing section 2a having the compartment 4 for the electrolytic cell 22.

Whenever medicament is to be dispensed, electric current is passed through the electrodes 22a, 22b of the electrolytic cell 24. The control of this electrical current may be effected by the on-off button 64 (FIG. 4), or automatically by the preprogrammable processor within housing section 70 (FIG. 5).

As current is applied to the electrodes 22a, 22b, a gas is generated by the electrolyte 22c between these two electrodes in accordance with the quantity of electricity applied, which may be prefixed or preprogrammed (e.g., the FIGS. 5, 6 embodiment). The so-generated gas increases the pressure within compartment 4 to thereby deform membrane 24 of compartment 4, as well as membrane 28 of the medicament compartment 6, to increase the volume of compartment 4 and to decrease the volume of compartment 6. This decrease in the volume of compartment 6 forces medicament out through the discharge opening 8, control valve 10 and feed tube 12, to the patient, who is thereby supplied medicament at a rate corresponding to the amount of electrical current applied to the electrolytic cell 22. Should any gas generated in compartment 4 permeate through membrane 24, e.g., by small holes in membrane 24, the protrusions or ribs 24a formed in the outer surface of membrane 24 will vent such leaking gas to the atmosphere, thereby preventing any such gas from entering the medicament compartment 6.

When compartment 4 will have expanded to its maximum volume, e.g., engaging the inner face of the upper wall 26 of housing section 2b, the pressure within compartment 4 will tend to increase by the further generation of gas. This will cause bellows 30 to expand, until it engages switch operator 32 to actuate switch 34 and thereby to terminate the further supply of electrical current to the electrolytic cell 22.

As described earlier, the dispenser may be primed by piecing a section of wall 20 by the needle of a syringe filled with a gas for introducing gas into compartment 4 in order to purge compartment 6 of air. In addition, control valve 10, and particularly its spring-urged valve member 46, blocks communication between the medicament chamber 6 and the feed tube 12 until a positive pressure has been built up in chamber 6, sufficient to overcome spring 50. This arrangement thus fixes the feeding rate, and also prevents rapid flow of medicament from chamber 6 to the feed tube 12 by siphonic action, for example should the outer end of the feed tube 12 be located below the level of the medicament chamber 6.

It will be seen that all three housing sections 2a, 2b and 2c, may be constructed as separate disposable units. Thus, housing section 2a can be replaced by a new section containing a fresh supply of the electrolyte; housing section 2b may be replaced by a new section to provide a new supply of medicament to be dispensed; and housing section 2c may be replaced by a new section to include a fresh supply of batteries.

While the invention has been described with respect to a preferred embodiment, including several variations, it will be appreciated that many other variations, modifications and applications of the invention may be made.

What is claimed is:

1. A liquid material dispenser, comprising:
   a rigid housing having a flexible partition therein defining first and second compartments on opposite sides of said partition; and
   an electrolytic cell in said first compartment capable of generating a gas when energized by a source of electric current in order to expand said first compartment and thereby to contract said second compartment;
   said second compartment being capable of containing a liquid material and including a discharge opening for dispensing said liquid material upon contraction of said second compartment in accordance with the rate of generation of said gas;
   said rigid housing being made of two separable sections each for housing one of said compartments;
   each of said two housing sections containing a membrane, the membranes of the two housing sections contacting each other when the two sections are attached to each other in the operative condition of the dispenser and together constitute said flexible partition;
   at least one of said membranes being formed with protrusions facing the other membrane to define a space between the two membranes, which space is vented to the atmosphere to prevent any gas generated in said first compartment from entering said second compartment.

2. The dispenser according to claim 1, wherein said first compartment carries a sensor for sensing a predetermined maximum pressure in said first compartment and effective, in response thereto, to terminate the electrical energization of the electrolytic cell.

3. The dispenser according to claim 1, wherein said electrolytic cell comprises a pair of flexible metal screens serving as electrodes and connectible to the source of electric current, and an electrolyte between said metal screens.

4. The dispenser according to claim 3, wherein said flexible metal screens are of stainless steel.

5. The dispenser according to claim 3, wherein said electrolyte includes sodium bicarbonate.

6. The dispenser according to claim 3, wherein said electrolyte includes copper sulphate.

7. The dispenser according to claim 1, wherein said first compartment comprises a wall pierceable by the needle of a syringe filled with air for introducing air into said first compartment in order to purge the second compartment of air when priming the dispenser.

8. The dispenser according to claim 1, wherein said second compartment further includes a venting opening permeable by air but not by liquid.

9. The dispenser according to claim 1, wherein said housing further includes a power supply and control circuitry for controlling the energization of the electrolytic cell.

10. The dispenser according to claim 9, wherein said control circuitry includes a preprogrammable processor for preprogramming the rates and times of energization of the electrolytic cell, and thereby of the dispensing of the liquid material from the second compartment.

11. A liquid material dispenser, comprising:
a rigid housing having a flexible partition therein defining first and second compartments on opposite sides of said partition; and
an electrolytic cell in said first compartment capable of generating a gas when energized by a source of electric current in order to expand said first compartment and thereby to contract said second compartment;
said second compartment being capable of containing a liquid material and including a discharge opening for dispensing said liquid material upon contraction of said second compartment in accordance with the rate of generation of said gas;
said rigid housing being made of two separable sections each for housing one of said compartments;
each of said two housing sections containing a membrane, the membranes of the two housing sections contacting each other when the two sections are attached to each other in the operative condition of the dispenser and together constituting said flexible partition;
said two housing sections being attachable to each other by a snap-on connection including projections carried by one of the sections snappable into recesses formed in the other of the sections.

12. The dispenser according to claim 11, wherein said projections carried by one section are formed at the other tips of a plurality of flexible fingers carried by said one section.

13. The dispenser according to claim 12, wherein said flexible fingers are carried by the section including said second compartment for containing the liquid material to be dispensed.

14. A liquid material dispenser, comprising:
a rigid housing having a flexible partition therein defining first and second compartments on opposite sides of said partition; and
an electrolytic cell in said first compartment capable of generating a gas when energized by a source of electric current in order to expand said first compartment and thereby to contract said second compartment;
said second compartment being capable of containing a liquid material and including a discharge opening for dispensing said liquid material upon contraction of said second compartment in accordance with the rate of generation of said gas;
said first compartment carrying a sensor for sensing a predetermined maximum pressure in said first compartment and effective, in response thereto, to terminate the electrical energization of the electrolytic cell;
said sensor comprising a chamber on a wall of said first compartment and expansible in accordance with the pressure in said first compartment, and an electrical switch operated by said expansible chamber for terminating the electric energization of the electrolytic cell.

15. The dispenser according to claim 14, wherein said chamber projection is in the form of a bellows whose interior communicates with the interior of said first compartment.

16. The dispenser according to claim 14, wherein said second compartment includes a control valve comprising a valve member and a spring normally urging the valve member to close said discharge opening, the valve member being movable to its open position upon the generation of pressure in said second compartment sufficient to overcome the force of said spring.

17. A liquid material dispenser, comprising:
a rigid housing having a flexible partition therein defining first and second compartments on opposite sides of said partition; and
an electrolytic cell in said first compartment capable of generating a gas when energized by a source of electric current in order to expand said first compartment and thereby to contract said second compartment;
said second compartment being capable of containing a liquid material and including a discharge opening for dispensing said liquid material upon contraction of said second compartment in accordance with the rate of generation of said gas;
said second compartment including a control valve comprising a valve member and a spring normally urging the valve member to close said discharge opening, the valve member being movable to its open position upon the generation of pressure in said second compartment sufficient to overcome the force of said spring;
said control valve comprising a housing having a central bore communicating with the interior of said second compartment, and an annular recess around said central bore and communicating with said discharge opening, said valve member normally being urged by said spring to cover both said central bore and said annular recess.

* * * * *

UNITED STATES PATENT AND TRADEMARK OFFICE
CERTIFICATE OF CORRECTION

PATENT NO. : 5,090,963

DATED : February 25, 1992

INVENTOR(S) : Gross et al.

It is certified that error appears in the above-identified patent and that said Letters Patent is hereby corrected as shown below:

Column 4     Line 37, "spring 0" should be -- spring 50--.

Column 5     Line 53, "64" should be --62--.

Column 7     Line 65, "other" should be --outer--.

Signed and Sealed this

Eleventh Day of January, 1994

Attest:

BRUCE LEHMAN

Attesting Officer            Commissioner of Patents and Trademarks